United States Patent
Cordi et al.

(10) Patent No.: US 7,262,189 B2
(45) Date of Patent: Aug. 28, 2007

(54) BENZOTHIAZINE AND BENZOTHIADIAZINE DERIVATIVES, METHOD FOR PREPARING SAME AND PHARMACEUTICAL COMPOSITIONS CONTAINING SAME

(75) Inventors: Alex Cordi, Suresnes (FR); Patrice Desos, Bois-Colombes (FR); Pierre Lestage, La Celle Saint Cloud (FR)

(73) Assignee: Les Laboratoires Server, Courbevoie (FR)

( * ) Notice: Subject to any disclaimer, the term of this patent is extended or adjusted under 35 U.S.C. 154(b) by 19 days.

(21) Appl. No.: 10/499,164

(22) PCT Filed: Dec. 20, 2002

(86) PCT No.: PCT/FR02/04483

§ 371 (c)(1),
(2), (4) Date: Jun. 15, 2004

(87) PCT Pub. No.: WO03/053978

PCT Pub. Date: Jul. 3, 2003

(65) Prior Publication Data

US 2005/0065146 A1 Mar. 24, 2005

(30) Foreign Application Priority Data

Dec. 21, 2001 (FR) .................... 01/16620

(51) Int. Cl.
*C07D 513/04* (2006.01)
*A61K 31/542* (2006.01)
*A61P 25/24* (2006.01)

(52) U.S. Cl. ................ 514/222.8; 544/9; 514/215; 540/578

(58) Field of Classification Search ............ 544/9; 514/222.8, 215; 540/578
See application file for complete search history.

(56) References Cited

FOREIGN PATENT DOCUMENTS

| EP | 0692484 A | 1/1996 |
|---|---|---|
| EP | 1176148 A | 1/2002 |
| WO | WO9942456 | 8/1999 |

OTHER PUBLICATIONS

Alt et al. Current Pharmaceutical Design, 2005, 11, 1511-1527.*
Black et al Psychopharmacology (2005) 179: 154-163.*
Maskell, et al., *Br. J. Pharmacol*, 2003, 140, 1313-1319.
Aracava, et al., *JPET*, 2005, 312, 1195-1250.
Advokat, et al., *Neurosci. Biobehav. Rev.*, 1992, 16, 13-24.
Danysz, et al., *Behav. Pharmacol.*, 1995, 6, 455-474.
Lynch, *Neurobiology of Learning and Memory*, 1998, 70, 82-100.
Robbins, et al., *TRENDS in Pharmacological Sciences*, 2006, 27 (3), 141-148.
Bliss, et al., *Nature*, 1993, 361, 31-39.
Ito, et al., *Journal of Physiology*, 1990, 424, 533-543.
Cumin, et al., *Psychopharmacology*, 1982, 78, 104-111.
Arai, et al., *Brian Res.*, 1994, 638, 343-346.
Miu, et al., *Neuropharmacol.*, 2001, 40, 976-983.
Staubli, et al., *Proc. Natl. Acad. Sci.*, 1994, 91, 777-781.
Lebrun, et al., *European Journal of Pharmacology*, 2000, 401, 205-212.
Rao, et al., *Neuroscience Letters*, 2001, 298, 183-186.
Thompson, et al., *Proc. Natl. Acad. Sci.*, 1995, 92, 7667-7671.
Buccafusco, et al., *Neuropharmacol.*, 2004, 46, 10-22.
Porrino, et al., *PLOS Biology*, 2005, 3 (9), 1639-1652.
Ingvar, et al., *Exp. Neurol.*, 1997, 146, 553-559.
Lynch, et al., *Exp. Neurol.*, 1997, 145, 89-92.
Baudry, *Neurobiology of Learning and Memory*, 2001, 76, 284-297.
Day, et al., *Nature*, 2003, 424, 205-209.
Lynch, *Current Opinion in Pharmacology*, 2006, 6, 82-88.
Lin, et al., *Brain Research*, 2002, 955, 164-173.
Desai, et al., *Neuropharmacology*, 1995, 34 (2), 141-147.
Lockhart, et al., *European Journal of Pharmacology*, 2000, 401, 145-153.

(Continued)

*Primary Examiner*—Kahsay Habte
(74) *Attorney, Agent, or Firm*—Hueschen and Sage

(57) ABSTRACT

Compounds of formula (I):

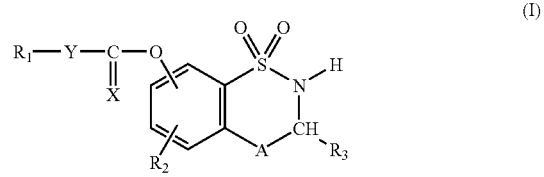

wherein:
$R_1$ represents aryl or heteroaryl,
$R_2$ represents hydrogen, halogen or hydroxy,
X represents oxygen or sulphur,
Y represents oxygen, sulphur or NR wherein R represents hydrogen or alkyl,
A represents $CR_4R_5$ or $NR_4$,
$R_3$ represents hydrogen, alkyl or cycloalkyl,
$R_4$ represents hydrogen or alkyl, or
A represents nitrogen and, together with adjacent —$CHR_3$—, forms the ring

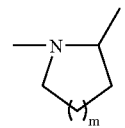

wherein m represents 1, 2 or 3,
$R_5$ represents hydrogen or halogen,
their isomers and also their addition salts
Medicaments.

6 Claims, No Drawings

OTHER PUBLICATIONS

Jhee, et al., *J. Clin. Pharmacol.*, 2006, 46, 424-432.
Roger, et al., *Soc. Neurosci. Abstr.*, 2004, Abstract No. 219.11.
Dicou, et al., *Brain Research*, 2003, 970, 221-225.
Bahr, et al., *Exp. Neurol.*, 2002, 174, 37-47.
Murray, et al., *JPET*, 2003, 306, 752-762.
O'Neill, et al., *European Journal of Pharmacology*, 2004, 486, 163-174.
O'Neill, et al., *CNS Drug Rev.*, 2005, 11 (1), 77-96.
Bai, et al., *Neuropharmacology*, 2003, 44, 1013-1021.
Lauterborn, et al., *J. of Neuroscicence*, 2000, 20 (1), 8-21.
Carrié, et al., *Soc. Neurosci. Abstr.*, 2005, Abstract No. 1018.4.
Lockhart, et al., *Soc. Neurosci. Abstr.*, 2004, Abstract No. 92.12.
Munoz, et al., *Soc. Neurosci. Abstr.*, 2004, Abstract No. 85.13.
Nibuya, et al., *J. of Neuroscience*, 1995, 15 (11), 7539-7547.
Dias, et al., *Neuropharmacology*, 2003, 45, 553-563.
Alt, et al., *Curr. Pharm. Des.*, 2005, 11 (12), 1511-1527.
Alt, et al., *Biochemical Pharmacology*, 2006, 71, 1273-1288.
Nakamura, et al., *Psychopharmacology*, 2001, 158, 205-212.
Li, et al., *Neuropharmacology*, 2001, 40, 1028-1033.
Knapp, et al., *European Journal of Pharmacology*, 2002, 440, 27-35.

* cited by examiner

BENZOTHIAZINE AND BENZOTHIADIAZINE DERIVATIVES, METHOD FOR PREPARING SAME AND PHARMACEUTICAL COMPOSITIONS CONTAINING SAME

The present invention relates to new benzothiazine and benzothiadiazine compounds, to a process for their preparation and to pharmaceutical compositions containing them.

It is now recognised that excitatory amino acids and, more especially, glutamate, play a crucial role in the physiological processes of neuronal plasticity and in the mechanisms underlying learning and memory. Pathophysiological studies have shown clearly that a deficiency in glutamatergic neurotransmission is closely associated with the development of Alzheimer's disease (Neuroscience and Biobehavioral reviews, 1992, 16, 13-24 Progress in Neurobiology, 1992, 39, 517-545).

Moreover, numerous studies over recent years have demonstrated the existence of excitatory amino acid receptor sub-types and their functional interactions (Molecular Neuropharmacology, 1992, 2, 15-31).

Among those receptors, the AMPA ("α-amino-3-hydroxy-5-methyl-4-isoxazole-propionic acid") receptor appears to be the receptor most implicated in the phenomena of physiological neuronal excitability and especially in those phenomena implicated in the processes of memorisation. For example, learning has been shown to be associated with an increase in the binding of AMPA to its receptor in the hippocampus, one of the cerebral regions essential to mnemocognitive processes. Similarly, nootropic agents, such as aniracetam, have very recently been described as modulating positively the AMPA receptors of neuronal cells (Journal of Neurochemistry, 1992, 58, 1199-1204).

In the literature, compounds of benzamide structure have been described as having that same mechanism of action and as improving mnesic performance (Synapse, 1993, 15, 326-329). Compound BA 74, in particular, is the most active of those new pharmacological agents.

Finally, patent specification EP 692 484 describes a benzothiadiazine compound having a facilitatory action on AMPA flux and patent application WO 99/42456 describes, inter alia, a number of benzothiadiazine compounds as modulators of AMPA receptors.

In addition to being new, the benzothiazine and benzothiadiazine compounds forming the subject-matter of the present invention surprisingly exhibit pharmacological activities in respect of AMPA flux that are clearly superior to those of the compounds of similar structure described in the prior art. They are useful as AMPA modulators in the treatment or prevention of mnemocognitive disorders associated with age, with anxiety or depressive syndromes, with progressive neurogenerative diseases, with Alzheimer's disease, with Pick's disease, with Huntington's chorea, with schizophrenia, with sequelae of acute neurodegenerative diseases, with sequelae of ischaemia and with sequelae of epilepsy.

The present invention relates more specifically to compounds of formula (I):

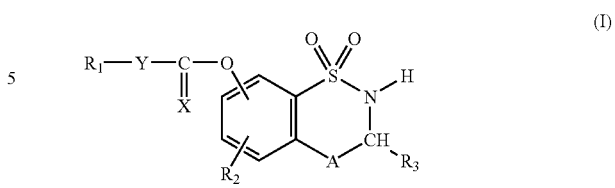

wherein:
$R_1$ represents an aryl or heteroaryl group,
$R_2$ represents a hydrogen atom, a halogen atom or a hydroxy group,
X represents an oxygen atom or a sulphur atom,
Y represents an oxygen atom, a sulphur atom or an NR group wherein R represents a hydrogen atom or a linear or branched ($C_1$-$C_6$)alkyl group,
A represents a $CR_4R_5$ group or an $NR_4$ group,
$R_3$ represents a hydrogen atom, a linear or branched ($C_1$-$C_6$)alkyl group or a ($C_3$-$C_7$)-cycloalkyl group,
$R_4$ represents a hydrogen atom or a linear or branched ($C_1$-$C_6$)alkyl group, or A represents a nitrogen atom and, together with the adjacent —$CHR_3$— group, forms the ring

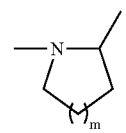

wherein m represents 1, 2 or 3,
$R_5$ represents a hydrogen atom or a halogen atom,
to their isomers and to their addition salts with a pharmaceutically acceptable acid or base, it being understood that:
"aryl group" is understood to mean an aromatic monocyclic group, or a bicyclic group in which at least one of the rings is aromatic, optionally substituted by one or more identical or different groups: halogen, linear or branched ($C_1$-$C_6$)alkyl, linear or branched ($C_1$-$C_6$)alkoxy, linear or branched ($C_1$-$C_6$)perhaloalkyl, linear or branched ($C_1$-$C_6$) perhaloalkoxy, hydroxy, cyano, nitro, amino (optionally substituted by one or more linear or branched ($C_1$-$C_6$) alkyl groups), aminosulphonyl (optionally substituted by one or more linear or branched ($C_1$-$C_6$)alkyl groups), ($C_1$-$C_6$)alkylsulphonylamino, or phenyl (optionally substituted by one or more identical or different groups: halogen, linear or branched ($C_1$-$C_6$)alkyl, linear or branched ($C_1$-$C_6$)perhaloalkyl, hydroxy or linear or branched ($C_1$-$C_6$)alkoxy),
"heteroaryl group" is understood to mean an aromatic monocyclic group, or a bicyclic group in which at least one of the rings is aromatic, containing one, two or three identical or different hetero atoms selected from nitrogen, oxygen and sulphur, optionally substituted by one or more identical or different groups: halogen, linear or branched ($C_1$-$C_6$)alkyl, linear or branched ($C_1$-$C_6$)alkoxy, linear or branched ($C_1$-$C_6$)perhaloalkyl, linear or branched ($C_1$-$C_6$) perhaloalkoxy, hydroxy, cyano, nitro, amino (optionally substituted by one or more linear or branched ($C_1$-$C_6$)

alkyl groups), aminosulphonyl (optionally substituted by one or more linear or branched ($C_1$-$C_6$)alkyl groups), or ($C_1$-$C_6$)alkylsulphonylamino.

Among the pharmaceutically acceptable acids there may be mentioned, without implying any limitation, hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, methanesulphonic acid, camphoric acid, etc.

Among the pharmaceutically acceptable bases there may be mentioned, without implying any limitation, sodium hydroxide, potassium hydroxide, triethylamine, tert-butylamine, etc.

The preferred aryl group is the phenyl group.

The preferred $R_2$ group is the hydrogen atom.

A preferably represents an $NR_4$ group or represents a nitrogen atom and, together with the adjacent —$CHR_3$— group, forms the ring

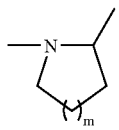

wherein m preferably represents the number 1.

Y preferably represents an oxygen atom or a sulphur atom.

The invention relates also to a process for the preparation of compounds of formula (I).

The process for the preparation of compounds of formula (I) wherein A represents an $NR_4$ group or A represents a nitrogen atom and, together with the adjacent $CHR_3$ group, forms the ring

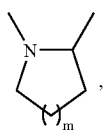

wherein m represents 1, 2 or 3, is characterised in that there is used as starting material a compound of formula (II):

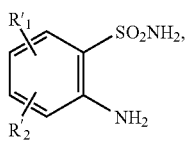

wherein:
$R'_1$ represents a linear or branched ($C_1$-$C_6$)alkoxy group,
$R'_2$ represents a hydrogen atom, a halogen atom or a linear or branched ($C_1$-$C_6$)alkoxy group,
which is:
(a) either reacted with the acid chloride of formula (III) in the presence of a base, in a tetrahydrofuran or acetonitrile medium:

Cl—CH$_2$—(CH$_2$)$_m$—CH$_2$—COCl    (III), wherein m is as defined for formula (I),
to yield the compound of formula (IV):

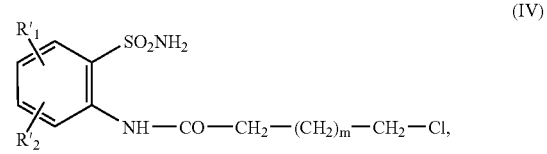

wherein $R'_1$, $R'_2$ and m are as defined hereinbefore,
which is then cyclised in basic medium to yield the compound of formula (V):

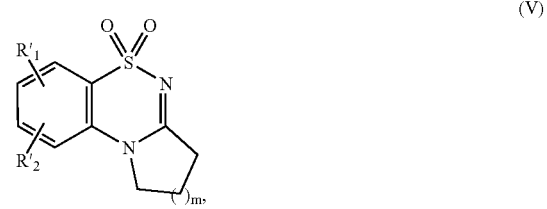

wherein $R'_1$, $R'_2$ and m are as defined hereinbefore,
which is subjected to reduction, in alcoholic or dimethylformamide medium, in the presence of sodium borohydride, to yield the compound of formula (VI):

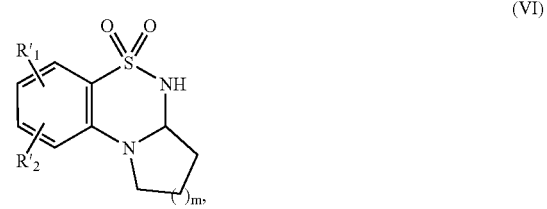

wherein $R'_1$, $R'_2$ and m are as defined hereinbefore,
which is subjected to the action of boron tribromide to yield the compound of formula (VII):

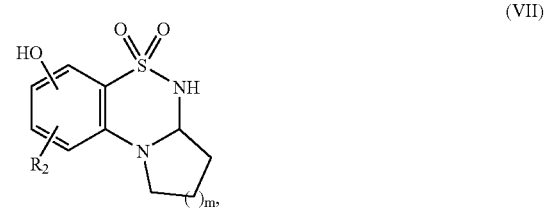

wherein m is as defined hereinbefore,
(b) or cyclised
in the presence of an amidine of formula (VIII):

wherein:
R₃ is as defined for formula (I),
to yield the compound of formula (IX):

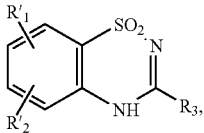
(IX)

wherein R'₁, R'₂ and R'₃ are as defined hereinbefore,
which is:
either reduced with a metallic hydride
to yield the compound of formula X):

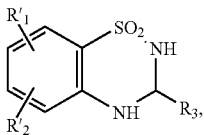
(X)

wherein R'₁, R'₂ and R'₃ are as defined hereinbefore,
or alkylated by the action of a strong base in the presence of an alkylating agent R'₄X wherein R'₄ represents a linear or branched (C₁-C₆)alkyl group and X represents a halogen atom, and then reduced
to yield the compound of formula (XI):

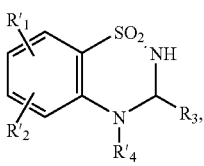
(XI)

wherein R'₁, R'₂, R₃ and R'₄ are as defined hereinbefore, or
in the presence of an aldehyde of formula (XII):

(XII)

wherein R₃ is as defined for formula (I),
to yield the compound of formula (X) described above,
the group R'₁ and the group R'₂, when it represents a linear or branched (C₁-C₆)alkoxy group, of which compound of formula (X) or (XI) are converted to hydroxy groups to yield the compound of formula (XIII):

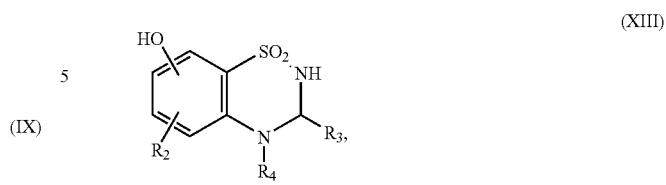
(XIII)

wherein R₂, R₃ and R₄ are as defined for formula (I),
which compound of formula (VII) or (XIII) is reacted with a compound of formula (XIVa):

(XIVa)

wherein R₁, X are as defined for formula (I), and Y' represents an oxygen atom, a sulphur atom or an NR' group wherein R' represents a linear or branched (C₁-C₆) alkyl group,
or with a compound of formula (XIVb):

$$R_1-N=C=X \qquad (XIVb)$$

wherein R₁ and X are as defined for formula (I),
to yield the compound of formula (I/a₁) or (I/a₂), particular cases of the compounds of formula (I):

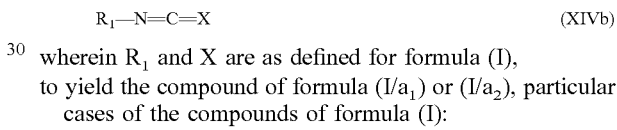
(I/a₁)

wherein X, Y, R₁, R₂, R₃ and R₄ are as defined for formula (I),

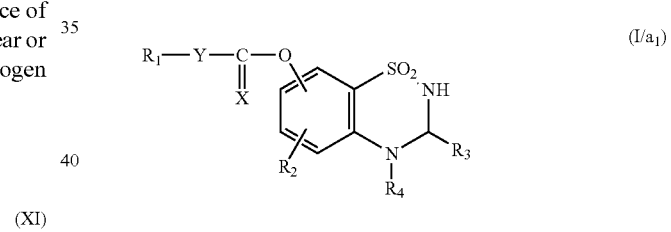
(I/a₂)

wherein X, Y, R₁, R₂ and m are as defined for formula (I),
which compounds of formula (I/a₁) or (I/a₂):

are, if necessary, purified according to a conventional purification technique, are optionally separated into the isomers according to a conventional separation technique and are converted, if desired, into their addition salts with a pharmaceutically acceptable acid or base.

The process for the preparation of compounds of formula (I) wherein A represents a CR₄R₅ group is characterised in that there is used as starting material a compound of formula (XV):

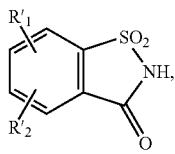
(XV)

wherein:
R'$_1$ represents a linear or branched (C$_1$-C$_6$)alkoxy group,
R'$_2$ represents a hydrogen atom, a halogen atom or a linear or branched (C$_1$-C$_6$)alkoxy group,
which is subjected to the action of chloroacetone in the presence of a mineral base in dimethylformamide medium to yield the compound of formula (XVI):

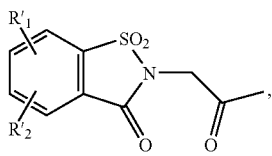
(XVI)

wherein R'$_1$ and R'$_2$ are as defined hereinbefore,
which is subjected to rearrangement in basic medium to yield the compound of formula (XVII):

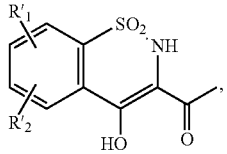
(XVII)

wherein R'$_1$ and R'$_2$ are as defined hereinbefore,
which is deacetylated by heating at reflux in benzene medium in the presence of an excess of ethylene glycol and a catalytic amount of p-toluenesulphonic acid to yield the compound of formula (XVIII):

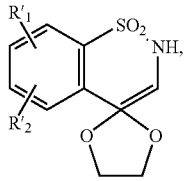
(XVIII)

wherein R'$_1$ and R'$_2$ are as defined hereinbefore,
which is subjected to hydrolysis in acid medium to yield the compound of formula (XIXa):

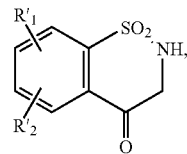
(XIXa)

wherein R'$_1$ and R'$_2$ are as defined hereinbefore,
of which, optionally, when R$_3$ is other than a hydrogen atom, the nitrogen atom is protected by a protecting group, and which then, after treatment with a strong base, is treated with a compound of formula R'$_3$—P,
wherein R'$_3$ represents a linear or branched (C$_1$-C$_6$)alkyl group or a (C$_3$-C$_7$)cycloalkyl group and P represents a leaving group,
to yield, after deprotection of the nitrogen atom, the compound of formula (XIX'a):

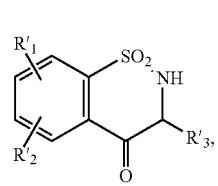
(XIX'a)

wherein R'$_1$, R'$_2$ and R'$_3$ are as defined hereinbefore,
which compound of formula (XIXa) or (XIX'a), represented by formula (XIX):

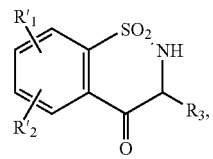
(XIX)

wherein R'$_1$ and R'$_2$ have the same meaning and R$_3$ is as defined for formula (I),
is:
either subjected to catalytic reduction to yield the compound of formula (XX):

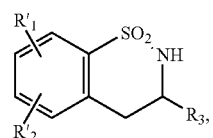
(XX)

wherein R'$_1$ and R'$_2$ are as defined hereinbefore,
or converted in alcohol by the action of a hydride the hydroxy group of which is converted to a halogen atom by the action of an appropriate reagent,
to yield the compound of formula (XXI):

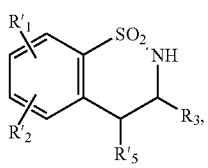

(XXI)

wherein R'₁ and R'₂ are as defined hereinbefore, R'₅ represents a halogen atom, or subjected to the action of an organomagnesium compound R'₄ MgBr wherein R'₄ represents a linear or branched ($C_1$-$C_6$)alkyl group, to yield the compound of formula (XIXb):

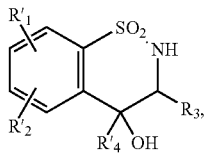

(XIXb)

wherein R'₁, R'₂ and R'₄ are as defined hereinbefore, which compound of formula (XIXb):

is either subjected to catalytic reduction to yield the compound of formula (XXII):

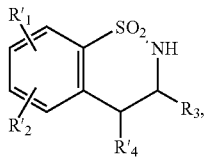

(XXII)

wherein R'₁, R'₂ and R'₄ are as defined hereinbefore, or the hydroxy group of which is converted to a halogen atom by the action of an appropriate reagent, to yield the compound of formula (XXIII):

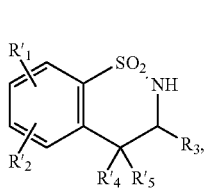

(XXIII)

wherein R'₁, R'₂ and R'₄ are as defined hereinbefore and R'₅ represents a halogen atom, the group R'₁ and the group R'₂, when it represents a linear or branched ($C_1$-$C_6$)alkoxy group, of which compounds of formulae (XX) to (XXIII) are converted to hydroxy groups to yield the compound of formula (XXIV):

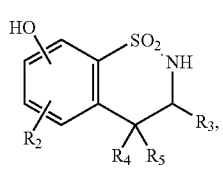

(XXIV)

wherein R₂, R₄ and R₅ are as defined for formula (I),
which compound of formula (XXIV) is reacted
with a compound of formula (XIVa):

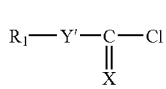

(XIVa)

wherein R₁, X are as defined for formula (I) and Y' represents an oxygen atom, a sulphur atom or an NR' group wherein R' represents a linear or branched ($C_1$-$C_6$)alkyl group, or with a compound of formula (XIVb):

(XIVb)

wherein R₁ and X are as defined for formula (I), to yield the compound of formula (I/b), a particular case of the compounds of formula (I):

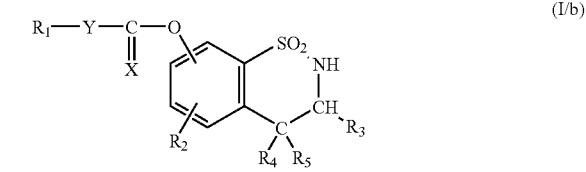

(I/b)

wherein X, Y, R₁, R₂, R₃, R₄, R₅ are as defined for formula (I), which is purified, if necessary, according to a conventional purification technique, is optionally separated into the isomers according to a conventional separation technique and is converted, if desired, into addition salts with a pharmaceutically acceptable acid or base.

The invention extends also to pharmaceutical compositions comprising as active ingredient a compound of formula (I) with one or more appropriate inert, non-toxic excipients. Among the pharmaceutical compositions according to the invention there may be mentioned more especially those which are suitable for oral, parenteral (intravenous or subcutaneous) or nasal administration, tablets or dragees, sublingual tablets, gelatin capsules, lozenges, suppositories, creams, ointments, dermal gels, injectable preparations, drinkable suspensions, etc. . . .

The dosage used can be adapted according to the nature and the severity of the disorder, the administration route and the age and weight of the patient. The dosage ranges from 1 to 500 mg per day in one or more administrations.

The following Examples illustrate the invention but do not limit it in any way.

The starting materials used are known products or products prepared according to known procedures.

The structures of the compounds described in the Examples were determined according to customary spectrophotometric techniques (infra-red, NMR, mass spectrometry . . . ).

EXAMPLE 1

5,5-Dioxido-2,3,3a,4-tetrahydro-1H-pyrrolo[2,1-c][1,2,4]benzothia-diazin-7-yl phenyl carbonate Step A: N-[2-(Aminosulphonyl)-4-methoxyphenyl]-4-chlorobutanamide 144 mmol of triethylamine and then, dropwise, a solution containing 135 mmol of 4-chlorobutanoic acid chloride in 30 ml of tetrahydrofuran (THF), are added to a solution containing 96.4 mmol of 2-amino-5-methoxybenzenesulphonamide in 200 ml of THF. After stirring overnight at ambient temperature, the THF is evaporated off and the residue is taken up in water. Following extraction with ethyl acetate, the organic phase is washed and dried. After evaporation, the expected product is obtained in the form of an oil.

Step B: 5,5-Dioxido-7-methoxy-2,3-dihydro-1H-pyrrolo[2,1-c][1,2,4]benzo-thiadiazine The product obtained in the above Step is stirred overnight at ambient temperature in 320 ml of an aqueous 1N sodium hydroxide solution. After the addition of 50 ml of ethyl acetate and stirring vigorously, the expected product, which precipitates, is filtered off, rinsed and dried.

Step C: 5,5-Dioxido-7-methoxy-2,3,3a,4-tetrahydro-1H-pyrrolo[2,1-c][1,2,4]-benzothiadiazine 106.5 mmol of sodium borohydride are added to a suspension containing 35.5 mmol of the product obtained in the above Step in 40 ml of dimethylformamide (DMF). After stirring overnight at ambient temperature, the reaction mixture is cooled and then 150 ml of an iced solution of 1N hydrochloric acid are added to the above mixture. The expected product precipitates and is filtered off.

Melting point: 193-198° C.

Step D: 5,5-Dioxido-2,3,3a,4-tetrahydro-1H-pyrrolo[2,1-][1,2,4]benzothiadiazin-7-ol 79.3 mmol of boron tribromide are added dropwise to a suspension containing 26.7 mmol of the product obtained in the above Step in 350 ml of dichloromethane maintained at −60° C. under nitrogen. The temperature is maintained for one hour and then the whole returns to ambient temperature and is stirred overnight. After cooling the reaction mixture in an ice bath, 100 ml of water are added and the biphasic system which is formed is stirred vigorously. The suspension so formed is filtered. The white solid obtained is washed with water, with ether, and dried, yielding the expected product.

Melting point: 237-242° C.

Step E: 5,5-Dioxido-2,3,3a,4-tetrahydro-1H-pyrrolo[2,1-c][1,2,4]benzothia-diazin-7-yl phenyl carbonate 0.175 ml of triethylamine, 5 mg of 4-dimethylaminopyridine and, dropwise, 0.136 ml of phenyl chloroformate dissolved in 2 ml of dichloromethane ($CH_2Cl_2$), are added to a suspension containing 0.83 mmol of the compound described in the above Step in 30 ml of $CH_2Cl_2$. After stirring for one night at ambient temperature, the solution is washed with 1N hydrochloric acid and then with a saturated sodium chloride solution, dried and evaporated.

After taking up the residue in ether, the expected product is obtained by filtration.

Melting point: 197-198° C.

| Elemental microanalysis: | | | | |
|---|---|---|---|---|
| | C | H | N | S |
| % theoretical | 56.66 | 4.47 | 7.77 | 8.90 |
| % experimental | 56.44 | 4.55 | 7.61 | 9.02 |

The following Examples were obtained according to the procedure described in Example 1 using the appropriate starting materials.

EXAMPLE 2

O-(5,5-Dioxido-2,3,3a,4-tetrahydro-1H-pyrrolo[2,1-c][1,2,4]-benzothiadiazin-7-yl)O-phenyl thiocarbonate The expected product is obtained by replacing phenyl chloroformate in Step E with phenyl thionochloroformate.

Melting point: 252-254° C.

| Elemental microanalysis: | | | | |
|---|---|---|---|---|
| | C | H | N | S |
| % theoretical | 54.24 | 4.28 | 7.44 | 17.03 |
| % experimental | 53.55 | 5.02 | 7.39 | 17.47 |

EXAMPLE 3

O-(5,5-Dioxido-2,3,3a,4-tetrahydro-1H-pyrrolo[2,1-c][1,2,4]benzo-thiadiazin-7-yl)S-phenyl dithiocarbonate The expected product is obtained by replacing phenyl chloroformate in Step E with phenyl dithiochloroformate.

Melting point: 210-214° C.

| Elemental microanalysis: | | | | |
|---|---|---|---|---|
| | C | H | N | S |
| % theoretical | 52.02 | 4.11 | 7.14 | 24.51 |
| % experimental | 51.85 | 4.10 | 7.36 | 24.69 |

EXAMPLE 4

O-(5,5-Dioxido-2,3,3a,4-tetrahydro-1H-pyrrolo [2,1-c][1,2,4]benzo-thiadiazin-7-yl)O-(4-chlorophenyl) thiocarbonate The expected product is obtained by replacing phenyl chloroformate in Step E with 4-chlorophenyl thionochloroformate.

Melting point: 189-194° C.

| Elemental microanalysis: | | | | | |
|---|---|---|---|---|---|
| | C | H | N | S | Cl |
| % theoretical | 49.69 | 3.68 | 6.82 | 15.61 | 8.63 |
| % experimental | 49.39 | 3.64 | 7.02 | 16.20 | 9.70 |

EXAMPLE 5

O-(4-Ethyl-1,1-dioxido-3,4-dihydro-2H-1,2,4-benzothiadiazin-7-yl)O-phenyl thiocarbonate Step A: 7-Methoxy4H-1,2,4-benzothiadiazine 1,1-dioxide There is stirred for 1 night at 80° C. a suspension of 3.0 g of 2-amino-5-methoxybenzene-sulphonamide in the presence of 1.31 g of formamidine hydrochloride and 2.27 ml of triethylamine in 50 ml of toluene. The toluene is evaporated off in vacuo. The residue is taken up in water and the precipitate is filtered off.

Step B: 7-Methoxy4-ethyl4H-1,2,4-benzothiadiazine 1,1-dioxide 2.88 g of the product obtained in the above Step are added portion by portion to a suspension of 9 ml of DMF containing 570 mg of 60% NaH in mineral oil. The mixture is stirred for 30 min. until a black solution is obtained. 929 µl of iodoethane are then added dropwise thereto. Stirring is continued for 1 h and the reaction mixture is precipitated by adding water. The precipitate is filtered off and rinsed with water and then with ether to yield the expected product.

Step C: 7-Methoxy 4-ethyl-3,4-dihydro-2H-1,2,4-benzothiadiazine 1,1-dioxide 1.19 g of sodium borohydride is added to a suspension of 2.37 g of the product of the above Step in 40 ml of ethanol. The mixture gradually becomes homogeneous. After reaction for 1 h at ambient temperature, the mixture is cooled in an ice bath and neutralised by the addition of 1N HCl. The white precipitate is stirred for 15 min. and the title product is filtered off.

Step D: 4-Ethyl-3,4-dihydro-2H-1,2,4-benzothiadiazin-7-ol 1,1-dioxide 79.3 mmol of boron tribromide are added dropwise to a suspension containing 2 g of the product obtained in the above Step in 200 ml of dichloromethane maintained at −60° C. under nitrogen. The temperature is maintained for one hour and then the whole returns to ambient temperature and is stirred overnight. After cooling the reaction mixture in an ice bath, 100 ml of water are added and the biphasic system is stirred vigorously. The suspension so formed is filtered. The solid obtained is washed with water, with ether, and dried, yielding the expected product.

Melting point: 214-218° C.

Step E: O-(4-Ethyl-1,1-dioxido-3,4-dihydro-2H-1,2,4-benzothiadiazin-7-yl)O-phenyl thiocarbonate The expected product is obtained according to the procedure described in Step E of Example 1, replacing phenyl chloroformate with phenyl thionochloroformate.

Melting point: 173-175° C.

| Elemental microanalysis: | | | | |
|---|---|---|---|---|
| | C | H | N | S |
| % theoretical | 52.73 | 4.43 | 7.69 | 17.60 |
| % experimental | 52.81 | 4.68 | 7.66 | 17.75 |

EXAMPLE 6

O-(4-Ethyl-1,1-dioxido-3,4-dihydro-2H-1,2,4-benzothiadiazin-7-yl) S-phenyl dithiocarbonate The expected product is obtained according to the procedure described in Example 5, replacing phenyl thionochloroformate in Step E with phenyl dithiochloroformate.

Melting point: 228-232° C.

| Elemental microanalysis: | | | | |
|---|---|---|---|---|
| | C | H | N | S |
| % theoretical | 50.50 | 4.24 | 7.36 | 25.28 |
| % experimental | 50.07 | 4.09 | 7.57 | 25.31 |

EXAMPLE 7

O-(4-Ethyl-1,1-dioxido-3,4-dihydro-2H-1,2,4-benzothiadiazin-7-yl) O-(4-chlorophenyl)thiocarbonate The expected product is obtained according to the procedure described in Example 5, replacing phenyl thionochloroformate in Step E with 4-chlorophenyl thionochloroformate.

Melting point: 155-156° C.

| Elemental microanalysis: | | | | | |
|---|---|---|---|---|---|
| | C | H | N | S | Cl |
| % theoretical | 48.18 | 3.79 | 7.02 | 16.08 | 8.89 |
| % experimental | 48.64 | 3.93 | 6.91 | 16.08 | 8.98 |

Pharmacological Study of the Products of the Invention

Study of the Excitatory Fluxes Induced by AMPA in Xenopus oocytes a-Method:

mRNAs are prepared from cerebral cortex of male Wistar rat by the guanidinium thiocyanate/phenol/chloroform method. The poly-(A$^+$) mRNAs are isolated by chromatography on oligo-dT cellulose and injected in an amount of 50 ng per oocyte. The oocytes are left to incubate for 2 to 3 days at 18° C. to allow expression of the receptors and are then stored at from 8 to 10° C.

Electrophysiological recording is carried out in a Plexiglass® chamber at from 20 to 24° C. in OR2 medium (J. Exp. Zool., 1973, 184, 321-334) by the 2-electrode "voltage-clamp" method, a 3rd electrode being placed in the bath to serve as reference.

All the compounds are administered via the incubation medium and the electric current is measured at the end of the period of administration. AMPA is used at a concentration of 10 µM. For each compound studied, the concentration that doubles (EC2×) or quintuples (EC5×) the intensity of the current induced by AMPA alone (5 to 50 nA) is determined.

The compounds of the invention potentiate very substantially the excitatory effects of AMPA and their activity is very clearly superior to that of the reference compounds.

The compound of Example 2, especially, has an EC2× of 1.8 µM and a EC5× of 9.6 µM.

Pharmaceutical Composition

Formulation for the preparation of 1000 tablets each comprising a dose of 100 mg

| | |
|---|---|
| compound of Example 1 | 100 g |
| hydroxypropyl cellulose | 2 g |
| wheat starch | 10 g |
| lactose | 100 g |
| magnesium stearate | 3 g |
| talc | 3 g |

The invention claimed is:

1. A compound selected from those of formula (I):

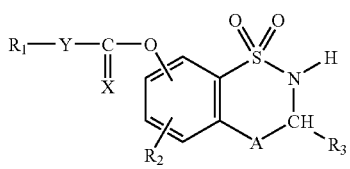

wherein:
- $R_1$ represents aryl or heteroaryl,
- $R_2$ represents hydrogen, halogen or hydroxy,
- X represents oxygen or sulphur,
- Y represents oxygen, sulphur or NR wherein R represents hydrogen or linear or branched ($C_1$-$C_6$)alkyl,
- A represents $NR_4$, and $R_3$ and $R_4$, together with the nitrogen and carbon atoms to which they are attached form a ring

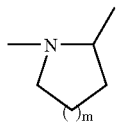

wherein m represents 1, 2 or 3, its isomers and addition salts thereof with a pharmaceutically acceptable acid or base, it being understood that:

"aryl" may be an aromatic monocyclic group, or a bicyclic group in which at least one of the rings is aromatic, each of those groups being optionally substituted by one or more identical or different halogen, linear or branched ($C_1$-$C_6$)alkyl, linear or branched ($C_1$-$C_6$)alkoxy, linear or branched ($C_1$-$C_6$)perhaloalkyl, linear or branched ($C_1$-$C_6$)-perhaloalkoxy, hydroxy, cyano, nitro, amino (optionally substituted by one or more linear or branched ($C_1$-$C_6$)alkyl), aminosulphonyl (optionally substituted by one or more linear or branched ($C_1$-$C_6$)alkyl), ($C_1$-$C_6$)alkylsulphonylamino, or phenyl (optionally substituted by one or more identical or different halogen, liner or branched ($C_1$-$C_6$)alkyl, linear or branched ($C_1$-$C_6$)perhaloalkyl, hydroxy or linear or branched ($C_1$-$C_6$)alkoxy), "heteroaryl" may be an aromatic monocyclic group, or bicyclic group in which at least one of the rings is aromatic, containing one, two or three identical or different hetero atoms selected from nitrogen, oxygen and sulphur, each of those groups being optionally substituted by one or more identical or different halogen, linear or branched ($C_1$-$C_6$)alkyl, linear or branched ($C_1$-$C_6$)alkoxy, linear or branched ($C_1$-$C_6$)perhaloalkyl, linear or branched ($C_1$-$C_6$)perhaloalkoxy, hydroxy, cyano, nitro, amino (optionally substituted by one or more linear or branched ($C_1$-$C_6$)alkyl), aminosulphonyl (optionally substituted by one or more linear or branched ($C_1$-$C_6$)alkyl), or ($C_1$-$C_6$)-alkylsulphonylamino.

2. A compound of claim 1 wherein $R_1$ represents aryl.

3. A compound of claim 1 wherein $R_2$ represents hydrogen.

4. A compound of claim 1 wherein m represents the number 1.

5. A pharmaceutical composition comprising as active principle an effective amount of a compound of claim 1, together with one or more pharmaceutically acceptable excipients or vehicles.

6. A method for treating a living animal body, including a human, afflicted with a condition selected from anxiety and depression, comprising the step of administering to the living animal body, including a human, an amount of a compound of claim 1 which is effective for alleviation of the condition.

* * * * *

UNITED STATES PATENT AND TRADEMARK OFFICE
CERTIFICATE OF CORRECTION

| | | |
|---|---|---|
| PATENT NO. | : 7,262,189 B2 | Page 1 of 1 |
| APPLICATION NO. | : 10/499164 | |
| DATED | : August 28, 2007 | |
| INVENTOR(S) | : Alex Cordi et al. | |

It is certified that error appears in the above-identified patent and that said Letters Patent is hereby corrected as shown below:

Title Page, item (73) Assignee: "Les Laboratoires Server" should be --Les Laboratoires Servier--.

Signed and Sealed this

Fourth Day of December, 2007

JON W. DUDAS
*Director of the United States Patent and Trademark Office*